US006455583B1

(12) United States Patent
Pflugfelder et al.

(10) Patent No.: US 6,455,583 B1
(45) Date of Patent: Sep. 24, 2002

(54) METHOD FOR TREATING MEIBOMIAN GLAND DISEASE

(75) Inventors: Stephen C. Pflugfelder; Balakrishna L. Lokeshwar, both of Miami; Marie Selzer, Fort Lauderdale, all of FL (US)

(73) Assignee: The University of Miami, Miami, FL (US)

( * ) Notice: Subject to any disclaimer, the term of this patent is extended or adjusted under 35 U.S.C. 154(b) by 0 days.

(21) Appl. No.: 09/307,182

(22) Filed: May 7, 1999

Related U.S. Application Data

(60) Provisional application No. 60/084,873, filed on May 8, 1998.

(51) Int. Cl.$^7$ ............................................... A01N 37/34
(52) U.S. Cl. .......................................... 514/528; 514/912
(58) Field of Search ................................. 514/528, 912

(56) References Cited

U.S. PATENT DOCUMENTS 5,523,297 A * 6/1996 Pruzanski et al. .......... 514/152

OTHER PUBLICATIONS

Caton, J., Evaluation of Periostat for Patient Management, Compendium, 1999, vol. 20, No. 5, pp. 451–462.
Mikino et al., "A Case of Rosacea Keratitis With Infectious Keratitis", Folia Ophthalmologica Japonica, vol. 48, (1997), pp. 1387–1391.
Ng et al., "Case Report—Ocular Rosacea", Singapore Medical Journal, vol. 37, No. 1 (1996) pp. 111–112.
Browning et al., "Ocular Rosacea", Survey of Ophthalmology, vol. 31, No. 3 (1986), pp. 145–158.
Salamon, Samuel M., "Tetracyclines in Ophthalmology", Survey of Ophthalmology, vol. 29, No. 4 (1985), pp. 265–275.
Quarterman et al., "Ocular Rosacea—Signs, Symptoms, and Tear Studies . . . ", Arch Dermatol, vol. 133, No. 1 (1997), pp. 49–54.
Zengin et al., "Meibomian Gland Dysfunction and Tear Film Abnormalities in Rosacea", Cornea, Vol. 14, No. 2 (1995), pp. 144–146.
Massey et al., "Effect of Drug Vehicle on Human Ocular Retention of Topically Applied Tetracycline", American Journal of Ophthalmology, vol. 81, No. 2 (1976), pp. 151–156.
Eady et al., "Modulation of Comedonal Levels of Interleukin–1 in Acne Patients Treated With Tetracyclines", Journal of Investigative Dermatology, vol. 101, No. 1 (1993), pp. 86–91.
Ballinger et al., "Tetracycline Inhibits Pro–inflammatory Cytokine Release From Mononuclear Cells", Gastroenterology, vol. 112, No. 4 (1997), p. A926, XP–002081054.
Medline Abstract 94254381, Heiligenhaus et al., 1994.*

* cited by examiner

*Primary Examiner*—Zohreh Fay
(74) *Attorney, Agent, or Firm*—Pillsbury Winthrop LLP (57) ABSTRACT

A method for treating a patient having meibomian gland disease, ocular irritation associated with delayed tear clearance, or recurrent corneal epithelial erosion, is disclosed. Preferably, the method concerns treatment of a patient with topical tetracycline, a derivative or analogue of tetracycline, or a chemically modified tetracycline (CMT). Oral administration of a CMT is also disclosed as part of the method for treating meibomian gland disease, ocular irritation associated with delayed tear clearance, or recurrent corneal epithelial erosion.

24 Claims, 8 Drawing Sheets

METHOD FOR TREATING MEIBOMIAN GLAND DISEASE

This application claims the benefit of provisional application 60/084,873 filed on May 8, 1998.

BACKGROUND OF THE INVENTION

Meibomian gland disease is the most common tear film and ocular surface disorder causing eye irritation. The incidence of the disease increases with age, and occurs in approximately 50% of patients with the skin disease, rosacea. A conservative estimate of the number of patients affected with this condition is 10 million in the United States alone. It has been reported that 15% of patients with ocular rosacea develop recurrent corneal epithelial erosions, a potentially sight-threatening problem.

Common complaints of patients suffering from meibomian gland disease include blurred or filmy vision, burning or foreign body sensations in the eye, photophobia, and pain severe enough to awaken the person from sleep. Although patients with this condition usually have normal production of aqueous tears by their lacrimal glands, their meibomian glands can atrophy and this is frequently accompanied by metaplasia of the ductal epithelium of these glands. Anterior erosion of the mucocutaneous junction of the eyelid is often noted, as well as eyelid and conjunctival infection, eyelid margin irregularity, corneal epithelial changes, and corneal vascularization.

The mechanisms responsible for the eyelid and ocular surface changes and irritation symptoms experienced by patients with meibomian gland disease were heretofore unknown. Therefore, previous treatments of meibomian gland disease were directed only to treatment of presumed infection of the eyelids or meibomian glands, or had particular disadvantages that made such treatments of little use for long periods of time. For example, patients with meibomian gland disease have been symptomatically treated with artificial tears, but these agents provide limited, if any, improvement. Topically applied steroids to the eyelids or ocular surface are effective as short-term pulse therapies. However, steroids are not good long-term solutions because of the potential side-effects e.g., cataract and glaucoma. Meibomian gland disease is currently not curable or reversible; therefore, patients with this condition must be treated for life.

Orally administered tetracyclines and tetracycline analogues (e.g., doxycycline and minocycline) having antibiotic activity are commonly and effectively used for prophylactic or therapeutic treatment of meibomian gland disease. The mechanism by which tetracyclines work in treating meibomian gland disease is not known, but some relief of symptoms has been reported. However, one disadvantage for using antimicrobially active tetracyclines or tetracycline analogues orally in the treatment of meibomian gland disease is that a high percentage of patients are unable to tolerate oral tetracyclines for extended periods of time. The intolerance to tetracyclines can manifest itself in gastrointestinal problems, e.g., epigastric pain, nausea, vomiting, and diarrhea, or other problems related to taking long-term oral antibiotics, such as mucosal candidiasis. At the present time there are no available long-term treatments of meibomian gland disease.

Recently, tetracycline and tetracycline analogues have been reported to have antimicrobial-inflammatory effects (e.g., reduction of IL-1 and nitric oxide production) and to inhibit synthesis and activation of MMPs. Tetracyclines have been reported to be effective in treating diseases where chronic inflammation and tissue destruction due to increased collagenase activity have been implicated. These diseases include rheumatoid arthritis, sterile corneal ulceration, and periodontitis.

Certain modifications of the chemical structure of tetracycline result in a tetracycline analogue which lacks antimicrobial activity. These non-antimicrobial, chemically modified tetracyclines (CMTs) retain their anti-inflammatory and anti-collagenolytic activities. Topical administration of antimicrobial tetracyclines or non-antimicrobial CMTs, or oral administration of non-antimicrobial CMTs represent a major advance in the therapy of patients having meibomian gland disease because both treatment modalities eliminate systemic toxicity and would allow lifetime administration of these therapeutic agents for this chronic disease.

BRIEF SUMMARY OF THE INVENTION

The subject invention concerns a class of agents and methods of using those agents for treatment of a patient having meibomian gland disease, including relief of symptoms or conditions associated with the disease, such as ocular irritation, delayed tear clearance, or recurrent corneal epithelial erosion. More specifically, the subject invention concerns agents and methods for decreasing ocular irritation, and surface inflammation, improving tear clearance, reducing tear IL-1α concentration, or inhibiting IL-1α-mediated matrix metalloproteinase activity which is increased in patients with meibomian gland disease or delayed tear clearance. The subject invention can thus be useful for reducing eye irritation, improving tear clearance, reducing IL-1α concentration in the tear fluid, or inhibiting MMP activity in the tear fluid of patients with delayed tear clearance and increased tear fluid IL-1α.

In a preferred embodiment, the subject invention concerns use of an effective amount of a topically administered antimicrobial tetracycline or tetracycline analogue, or a non-antimicrobial analogue of tetracycline. Non-antimicrobial tetracycline analogues are commonly referred to and accepted in the scientific literature as "chemically modified tetracyclines" (CMTs). These compounds, or compositions comprising those compounds, can be used for treating meibomian gland disease, ocular irritation associated with delayed tear clearance, or recurrent corneal epithelial erosion. Alternatively, CMTs can be administered orally for treating meibomian gland disease, ocular irritation associated with delayed tear clearance, or recurrent corneal epithelial erosion.

BRIEF DESCRIPTION OF THE DRAWINGS

Media=negative control; LPS=cultures treated with lipopolysaccharide for 24 h; LPS MP=cultures treated with LPS and the corticosteroid methylprednisolone for 24 h; LPS Doxy=cultures treated with LPS and doxycycline (5 µg/ml) for 24 h.

DETAILED DESCRIPTION OF THE INVENTION

This invention concerns, in a preferred embodiment, the use of topically applied antimicrobial tetracyclines, including tetracycline or a tetracycline analogue, or topically or orally administered chemically-modified tetracyclines (CMTs) for treatment of a patient having meibomian gland disease. According to the subject invention, treatment of a patient having meibomian gland disease includes reducing or reversing irritation symptoms, delayed tear clearance, recurrent corneal epithelial erosion oraqueousteardeficiency. The CMTs lack antimicrobial activity. For purposes of this invention, tetracycline and its analogues having antimicrobial activity are termed "antimicrobial tetracyclines" and the tetracycline analogues lacking antimicrobial activity are termed "CMTs".

We recently discovered that patients with meibomian gland disease have significantly delayed tear clearance, rapid tear break-up time (often instantaneous), and tear film instability. In addition, it was found that meibomian gland disease patients have significantly greater concentrations of the pro-inflammatory cytokine, interleukin I alpha (IL-1α) in their tear fluid.

IL-1α has been reported to have multiple biological effects, including increasing expression of adhesion molecules by vascular endothelial and epithelial cells that facilitate binding of inflammatory cells, inducing expression of chemotactic cytokines such as interleukin 8, stimulating production of prostaglandins that increase vascular permeability and pain, stimulating production of nitric oxide that causes vasodilation and redness, and stimulation of production of matrix-degrading enzymes, termed matrix metalloproteinases (MMPs), by several different cell types, including mucosal epithelium.

We found that the activity of one member of the MMP family, MMP-9 (also termed gelatinase B), is markedly increased in the tear fluid of patients with meibomian gland disease associated with rosacea, as compared to normal asymptomatic patients. In addition, activity of gelatinase B appears to be inversely correlated with tear clearance.

These data indicate that antimicrobial tetracyclines and tetracycline analogues and CMTs possess biological activities capable of neutralizing the inflammatory and matrix degrading factors that have been found to be strongly correlated with the development of ocular rosacea in our studies.

Advantageously, topically applied tetracyclines or CMTs can have greater efficacy because of the higher concentrations that can be achieved at the disease site. Because of their lack of antimicrobial-bacterial effect and greater therapeutic activity, CMTs can have fewer systemic or other side effects than tetracyclines, whether administered orally or topically.

Topical administration of a tetracycline analogue in an ointment (e.g., oxytetracycline) or in solution (e.g., doxycycline eye drops), to patients having meibomian gland disease associated with rosacea resulted in complete resolution of symptoms in 73% (8 of 11) of the patients treated with the tetracycline analogue ointment and more than 90% (10 of 11) of the patients treated with the tetracycline analogue solution.

Several patients who had previously used oral tetracycline stated that improvement in their symptoms was better with topically applied oxytetracycline than orally administered tetracycline. Three patients had moderate but not complete relief of symptoms. Three other patients experienced burning from the medication, one of which ceased treatment.

The tetracycline utilized in the present invention may be any of the readily available, pharmaceutically acceptable tetracyclines known in the medical art. Included in this group of tetracyclines are those such as chlortetracycline, which is marketed under the tradename Acronize, Aureocina, Aureomycin, Biomitsin, Biomycin, and Chrysomykine; Demeclyeycline marketed as Ledermycin, Detravis, Meciclin, and Mexocine; Doxycyline marketed as Vibramycin, Vibramycin Hyclace, Liomycin Vibradox, Panamycin, Titradox, Hydramycin, Tecacin; Lymecycline which is marketed as Armyl, Mucomycin, Tetramyl, Tetralysal; Methacycline which is marketed as Adriamicina, Cyclobiotic, Germicilclin, Globociclina, Megamycine, Pindex, Londomycin, Optimycin, Rondomycin; Minocycline which is marketed as Minocin, Klinomycin, Vectrin; Oxytetracycline which is marketed as Biostat, Oxacycline, Oxatets, Oxydon, Oxymycin, Oxytan, Oxytetracid, Ryomycin, Stezazin, Tetraject, Terramycin, Tetramel, Tetran, Dendarcin, Dendarcin; Rolitetracycline marketed as Bristacin, Reverin, Superciclin, Syntetrex, Syntetrin, Synotodecin, Tetraverin, Transcycline, Velacicline, Velacycline; and Tetracycline marketed as Achromycin, Ambramycin, Cyclomycin, Polycycline, Tetrabon, and Tetracyn.

The active salts which are formed through protonation of the dimethylamino group on carbon atom 4, exist as crystalline compounds and are very stable in water. However, these amphoteric antibiotics will crystallize out of aqueous solutions of their salts unless stabilized by an excess of acid. The hydrochloride salts are used most commonly for oral administration. Water soluble salts may be obtained also from bases such as sodium or potassium hydroxides but are not stable in aqueous solution, they are also formed with divalent and polyvalent metals.

The tetracyclines or CMTs used according to the present invention are preferably orally administered at a dosage level from about 10% to about 100%, and preferably about 20% to about 80% of the normal antibiotic therapeutic dose of the particular tetracycline compound being employed. By normal antibiotic therapeutic dose is meant the dosage of the particular tetracycline compound which is commonly used and recommended for the treatment of bacterial infection. Alternatively, sub-antimicrobial dose means a dose having no significant antimicrobial effect in vitro or invivo . More than 100% of the normal antibiotic therapeutic dose can be utilized in the method of the present invention. The normal antibiotic therapeutic dose of the tetracycline is, for the most part, well studied and well documented.

Tetracyclines and chemically modified tetracyclines for topical administration can be added to buffered and electrolyte balanced aqueous solutions, buffered and electrolyte balanced aqueous solutions with a lubricating polymer, mineral oil or petrolatum-based ointment, other oils, liposomes, cylcodextrins, sustained release polymers or gels in a range from 0.001 to 3% (weight per volume or weight per weight). These preparations can be administered to the preocular tear film or onto the eyelid skin or lid margin 1 to 6 times per day for a period up to the lifetime of the patient. For example, an eye drop solution comprising doxycycline as an active ingredient was prepared by dissolving pharmaceutical grade doxycycline hydrochloride powder in an electrolyte-balanced salt solution (BSS™, Alcon, Ft. Worth, Tex.) to a final concentration of 0.025%.

In a preferred embodiment, the compounds useful according to the subject invention are tetracyclines which have been chemically modified so as to substantially reduce or eliminate antimicrobial properties and increase their antimicrobial-inflammatory activity. Methods for reducing antimicrobial properties of a tetracycline are disclosed in *The Chemistry of the Tetracyclines*, Ch. 6, Mitscher, Ed., at p. 211. As pointed out by Mitscher, modification at positions 1, 2, 3, 4, 10, and 12a can lead to loss of antimicrobial activity. Such chemically modified tetracyclines (CMTs) are included in the preferred embodiment of the present invention, since they can be used without disturbing the normal microbial flora of the treated mammal as would happen with extended exposure to antimicrobial tetracyclines.

Preferable CMTs used according to the subject invention include those lacking a dimethylamino side chain at position 4. For example, 4-dedimethylamino-chlotetracycline, 4-dedimethylamino-5-oxytetracycline, 4-dedimethylamino-7-chlortetracycline, 4-hydroxy-4-dedimethylaminotetracycline, 4-dedimethylamino-2a-deoxytetracycline, 4-dedimethylamino-11-hydroxy-12a-deoxytetracycline, 4-dedimethylamino-7-dimethylaminotetracycline, 6-dimethyl-6-deoxy-4-dedimethylaminotetracycline, 6-o-deoxy-5-hydroxy-4-dedimethylaminotetracycline, 11a-chlortetracycline, 12a-deoxytetracycline, and the 2-nitrilo analogs of tetracycline.

The amount of tetracycline or CMT administered to effectively treat meibomian gland disease, ocular irritation associated with delayed tear clearance, or recurrent corneal epithelial erosion is an amount that significantly improves tear clearance, reduces IL-1α concentration in the tear fluids, or IL-1α mediated production of MMPs, or MMP activity. The maximal dosage for humans is the highest dosage that does not cause clinically important side effects. For the purpose of the present invention, side effects include clinically important disruption of the normal flora as well as toxic effectsto the eye surface.

The dosage of tetracyclines administered in the present invention is also additionally dependent upon the age and weight of the person being treated, the mode of administration, and the type and severity of the inflammatory or matrix-degrading disease being treated. For illustrative purposes, a suitable amount of the antimicrobial tetracycline, doxycycline, is 0.1–4.0 mg/kg/day. In the case of a non-antimicrobial tetracycline, for example, the dose for 4-dedimethylaminotetracycline can be 0.1–30 mg/kg/day. However, in either case, the preferred method of treatment includes tetracycline or CMT compositions administered topically to the eye in suitable pharmaceutical carriers. The pharmaceutical carrier may be in the form of a solution, suspension, ointment, gel, or other form suitable for topical administration of the tetracycline or topical or oral administration of CMT to the affected mammal. For oral administration, the CMTs utilized according to the subject invention can be formulated in the form of tablets, capsules, elixirs, or the like. Additionally, the tetracyclines or CMTs of the present invention can be reasonably incorporated into a.polymer carrier delivery system for use topically, subconjunctivally, or orally. In addition, other means of administration are contemplated, such as by injection, either intramuscularly or intravenously.

The following Examples describe in detail compositions and methods illustrative of the present invention. It will be apparent to those skilled in the art that many modifications, both of materials and methods, may be practiced without departing from the purpose and intent of this disclosure.

EXAMPLE 1

Identification of Increased IL-1α Concentrations in Meibomian Gland Disease Patients In one study, tear fluid concentrations of lnterleukin-1-alpha (IL-1α), Tumor Necrosis Factor-α (TNF-α), and Epidermal Growth Factor (EGF) in patients having ocular rosacea were compared with those concentrations in normal patients (controls).

Fourteen (14) patients with severe meibomian gland disease, facial rosacea, and symptoms of ocular irritation were examined for ocular surface disease, tear production and tear clearance rate (TCR). For meibomian gland disease assessment, meibomian glands were examined by slit lamp biomicroscopy and graded for the presence of orifice metaplasia, expressibility of meibum, and meibomian gland acinar dropout, as previously described and known from the scientific literature. Twelve (12) controls, frequency-matched for age, and fifteen (15) ideal normals were assessed using the same parameters.

Minimally stimulated tear samples (20 $\mu$l) were drawn from each subject and analyzed using a sandwich ELISA to detect IL-1α, TNF-α, and EGF. Sandwich ELISA assays for EGF, IL-1α and TNF-α were performed using commercial kits (R&D Systems, Minneapolis, Minn.). Prior to each analysis tears were extracted in a masked fashion by the laboratory technician from the saturated rods by centrifuging at 3,500 g for 5 minutes within the pipette tip.

The samples from both eyes of each patient were pooled. The rods and pipette tips were carefully removed and the tears aspirated (2 $\mu$l for EGF assay and 4 $\mu$l for IL-1α and TNF-α assays) and diluted in ELISA buffer (supplied by manufacturer) to a final volume of 200 $\mu$l. The tear samples were transferred to wells of microliter plate and the ELISA performed according to the instructions provided by the manufacturer. Cytokine concentrations were determined from the standard curve as described previously in the literature. The results of the cytokine concentration assays for each subject group are shown in Table 1 below.

TABLE 1

Inflammatory Cytokines in Tears

| Subject Group | Tumor Necrosis Factor-α (pg/ml) | Interleukin-1α (pg/ml) |
| --- | --- | --- |
| Rosacea patients | <10 pg/ml | 45.4 ± 4.6 |
| Age-matched controls | <10 pg/ml | 22.6 ± 5.0 (p = 0.003) |
| Ideal controls | <10 pg/ml | 17.1 ± 3.4 (p < 0.001) |

P values listed for each control group are derived from comparison of the mean value of that group with the mean value of the same variable in the rosacea group.

Figure 1:
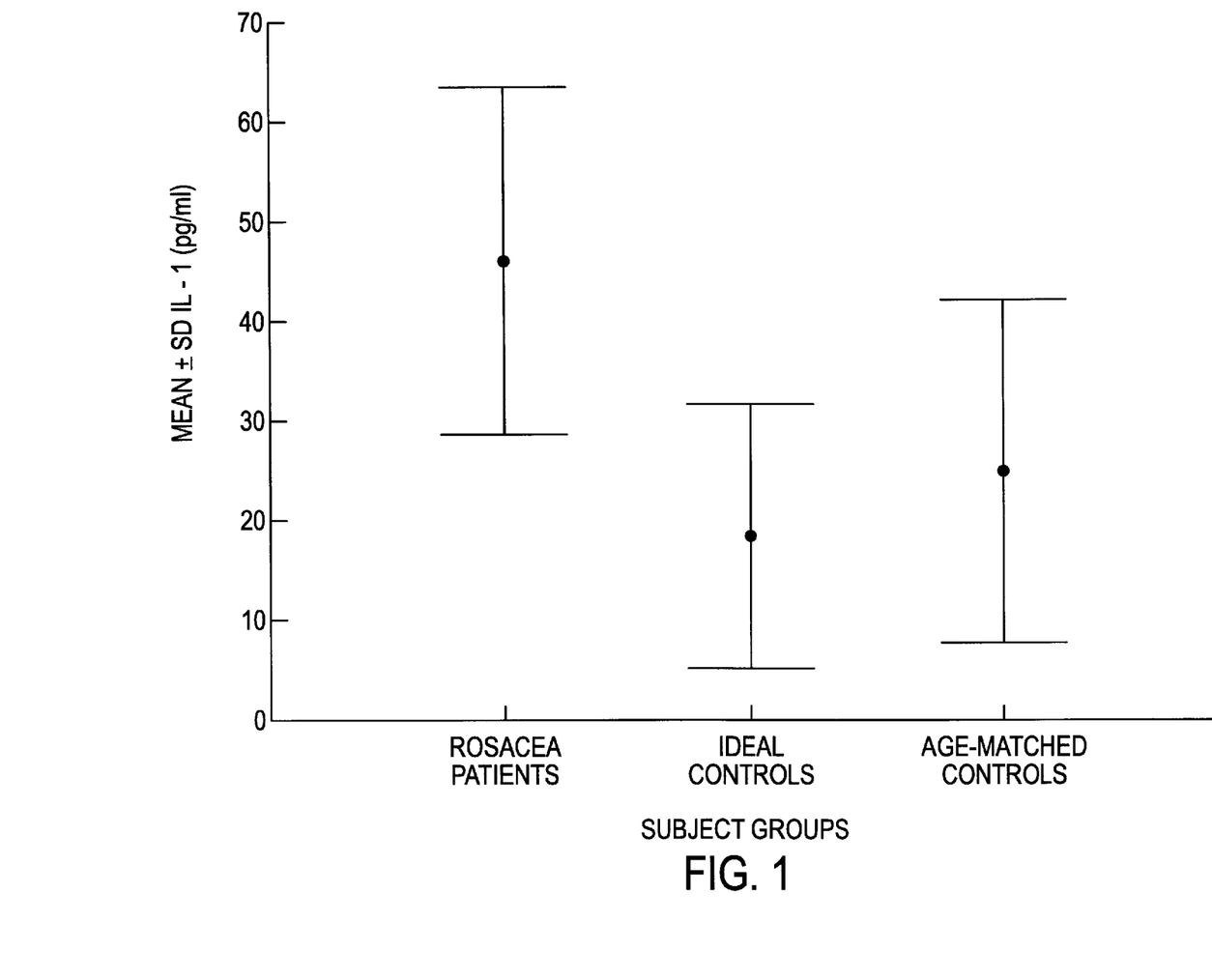
FIG. 1 shows IL-1α concentrations in tear fluid for rosacea patients, ideal controls, and age-matched control subject groups.

Tear IL-1α concentration was significantly higher in rosacea patients than in age-matched (p=0.003) and ideal normal controls (p<0.00 1)(FIG. 1). TNF-α was not detected in patients or controls, indicating levels of less than 10 pg/ml. EGF was not significantly higher in rosacea patients than in age-matched controls. Tear Clearance LN(TCR) was significantly lower in rosacea patients than in both age-matched (p=0.048) and ideal controls (p=0.002). Schirmer I scores were statistically lower in rosacea patients than ideal controls (p=0.013), but not age-matched controls. IL-1α was correlated inversely with tear clearance LN(TCR) (r=0.58 p<0.0001) and Schirmer I (r=−0.39, p=0.012).

It was concluded that concentrations of IL-1α are present in normal tears but are elevated in ocular rosacea, whereas TNF-α is not. The reduced tear clearance LN(TCR), its inverse correlation with IL-1α, and the absence of TNF-α the tears of these patients, suggests that the increased concentration of IL-1α observed, may be largely due to failure of clearance of cytokine normally produced at the ocular surface.

In summary, there is a differential increase in the level of the inflammatory cytokine IL-1α in the tear fluid in patients having ocular rosacea. Much of this elevation can be caused by reduced tear clearance, which can encourage tear stagnation and perpetuate ocular surface inflammation by stimulating production of inflammatory molecules.

EXAMPLE 2

Correlation of Gelatinase Activity with IL-1α Concentration and Tear Clearance

Tear fluorescein clearance was correlated with IL-1α concentration and 92 kD gelatinase (MMP 9) activity in the tears of patients. Thirteen patients with ocular rosacea (including 1 patient with recurrent epithelial erosion, 2 with recurrent peripheral corneal infiltrates and vascularization and 2 patients with epithelial basement membrane dystrophy) and 13 normal subjects with normal aqueous tear production and no irritation symptoms were evaluated. Tear fluorescein clearance was evaluated by measuring fluorescence in tear fluid collected from the inferior meniscus 15 minutes after instillation of 5 ml of 2% Na-fluorescein with a Cytofluor II. IL-1α was measured by ELISA using an R&D Systems kit. Gelatinase activity was evaluated by gelatin zymography, comparing tear activity to purified 92 kD gelatinase (MMP 9).

Figure 2:
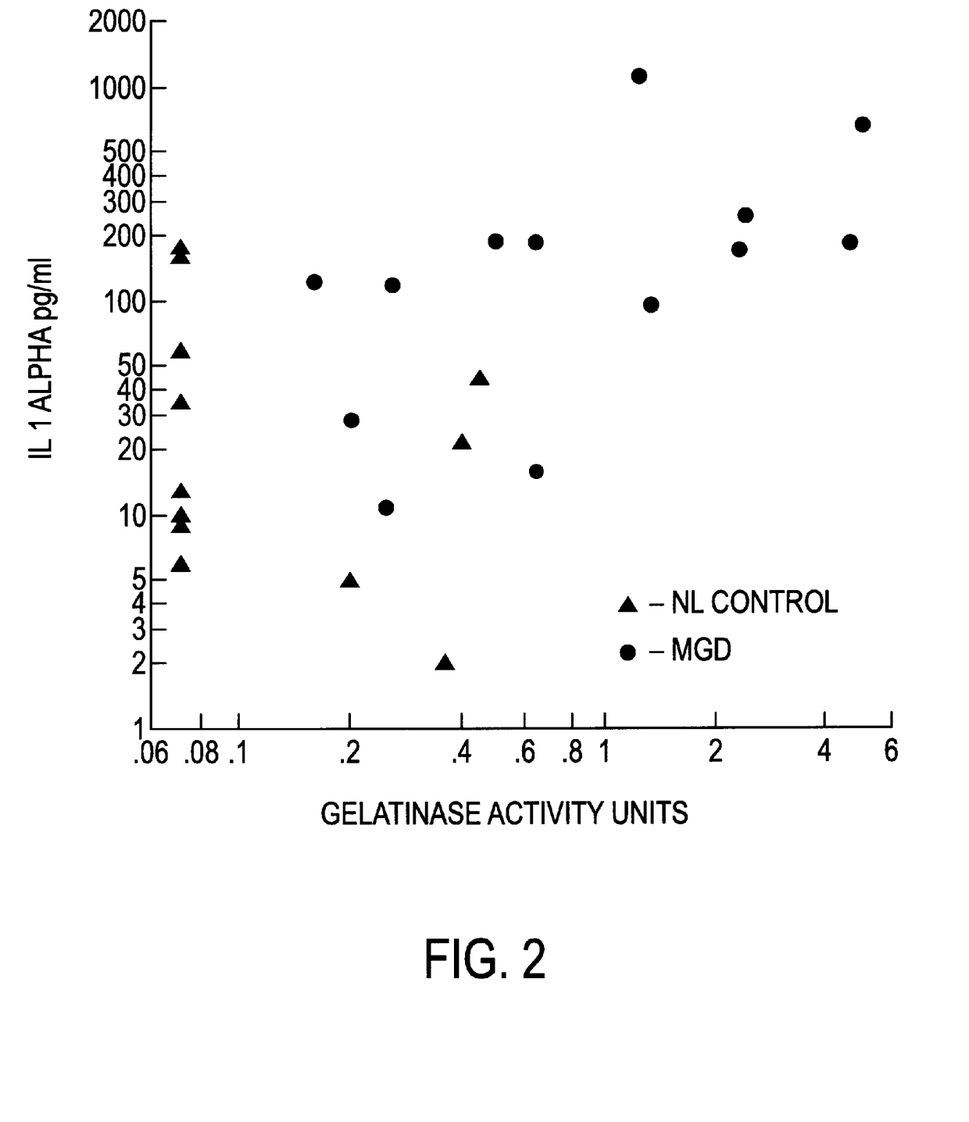
FIG. 2 shows gelatinase activity plotted against IL-α concentrations for normal control (NL) patients and meibomian gland disease (MGD) patients.
Figure 3:
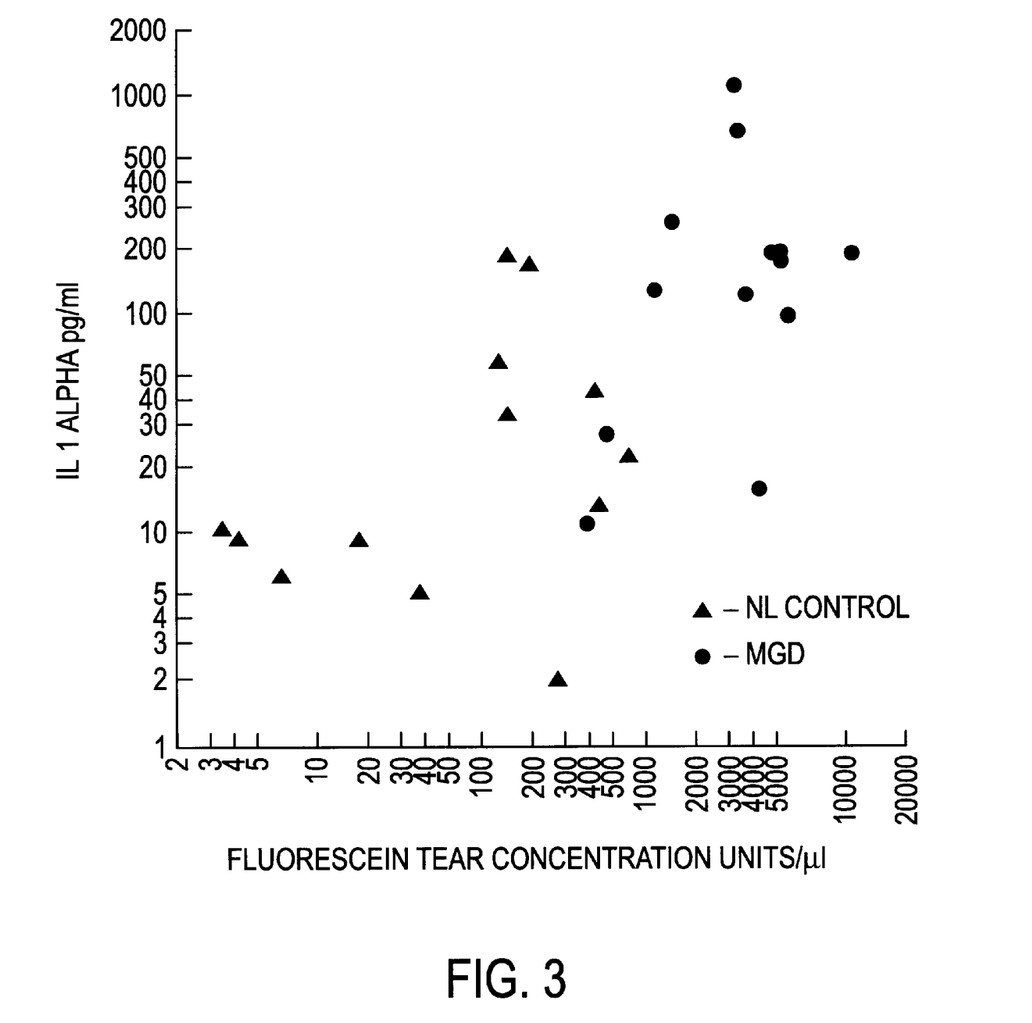
FIG. 3 shows fluorescein tear concentration plotted against IL-α concentration for normal control (NL) patients and meibomian gland disease (MGD) patients.
Figure 4:
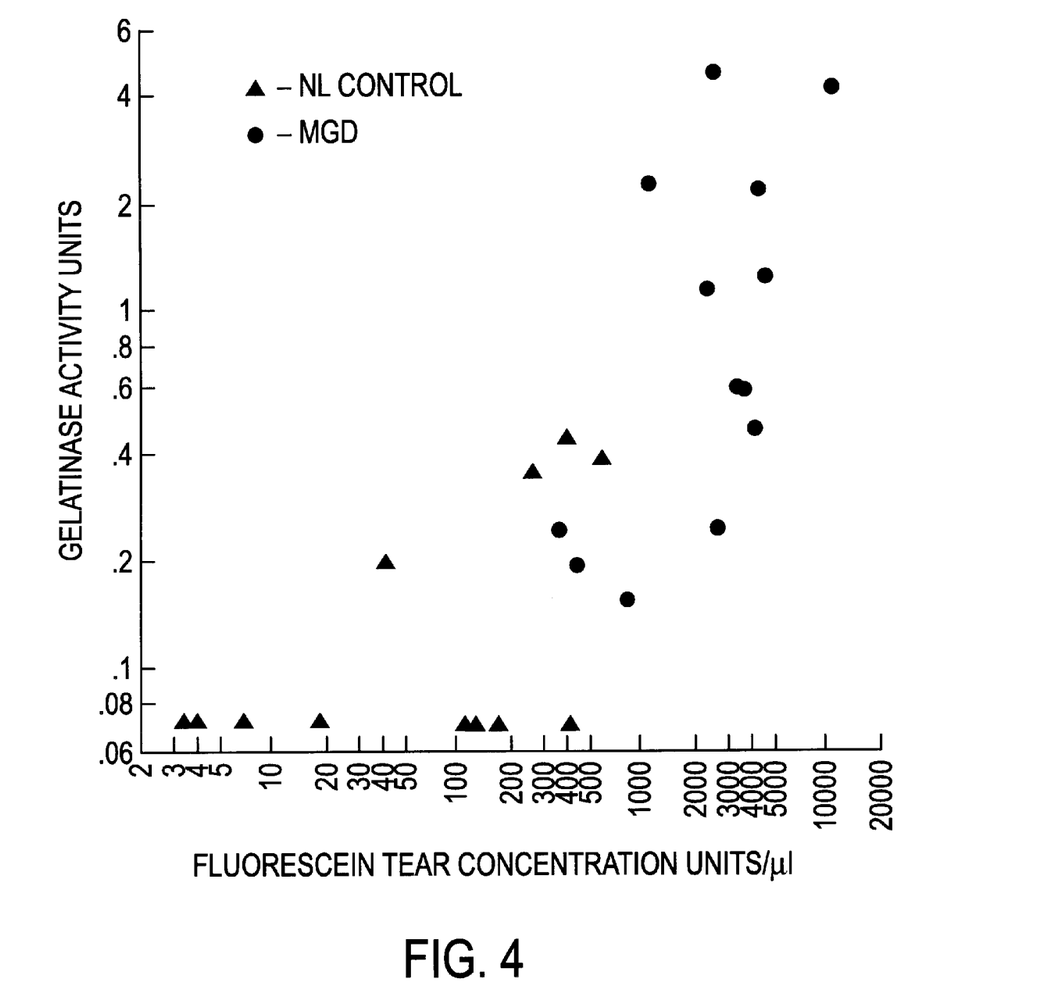
FIG. 4 shows fluorescein tear concentration plotted against gelatinase activity normal control (NL) patients and meibomian gland disease (MGD) patients.

Compared to normal controls, patients with ocular rosacea had greater delay of fluorescein clearance (p<0.001), higher tear IL-1α concentration (p<0.001), and greater 92 kD gelatinase activity (p<0.001). Tear IL-1α concentration was correlated with gelatinase activity (rho=0.58, p<0.002) (FIG. 2); delayed tear clearance was correlated with elevated tear IL-1α concentration (rho=0.84, p<0.001) (FIG. 3) and increased gelatinase activity (rho=0.84, p<0.001)(FIG. 4).

EXAMPLE 3

Reduced Tear Clearance in Ocular Irritation

Reduced tear clearance is commonly found in most patients with ocular irritation irrespective of the patient's tear production. Forty (40) abnormal patients presenting with a chief complaint of ocular irritation and forty (40) asymptomatic controls of similar age distribution were used to correlate and compare a new method of measuring tear fluorescein clearance and the Schirmer 1 test with the severity of ocular irritation symptoms, presence of meibomian gland disease, corneal fluorescein staining scores, and corneal and conjunctival sensitivity. All subjects completed a symptom questionnaire, a baseline ocular examination, fluorescein clearance test (FCT) and Schirmer test.

Methods. The fluorescein clearance test (FCT) was performed by measuring the fluorescein concentration in minimally-stimulated tear samples collected from the inferior tear meniscus 15 minutes after instillation of 5 µl of 2% sodium fluorescein with a Cytofluor II fluorophotometer. Severity of ocular irritation was assessed with a symptom questionnaire.

Schirmer 1 test, biomicroscopic meibomian gland evaluation, corneal fluorescein staining score and corneal and conjunctival sensation scores with the Cachet-Bonnet anesthesiometer were assessed in all subjects.

Results. Irritation symptoms correlated with higher log tear fluorescein concentration (symptomatic 3.08+/−0.62 units/µl, normal control 1.89+/−0.7 units/µl, p<0.005) and lower Schirmer 1 test scores (symptomatic 12.6 mm, normal control 22.3 mm, p<0.005). The fluorescein clearance test showed greater predictive value for identifying ocular irritation than the Schirmer 1 test.

EXAMPLE 4

Doxycycline Therapy Improves Tear Clearance and Reduces IL-1 Concentration in the Tear Fluid Six patients were treated with oral doxycycline 50 mg orally twice a day for 3 weeks. An improvement in irritation symptoms was observed in 5 of 6 patients. Additionally, decreased conjunctival hyperemia and corneal fluorescein staining was observed in all patients. An improvement in fluorescein clearance was noted in 5 of 6 patients and reduction of tear fluid IL-1 concentration was also observed in 5 of 6 patients. These findings indicate that tetracyclines reduce two of the significant risk factors for ocular irritation in patients with meibomian gland disease.

EXAMPLE 5

Resolution of Symptoms of Meibomian Gland Disease by Topical Administration of Oxytetracycline Eleven ( 11) patients with ocular irritation symptoms due to meibomian gland disease associated with rosacea and delayed tear clearance were treated with a commercially available oxytetracycline ointment (Terak, Akorn Pharmaceuticals) as a topical administration to the ocular surface or the eyelids. Seventy-three percent (73%) of these patients had complete resolution of irritation symptoms. See Table 2 below.

TABLE 2

Patients with Ocular Rosacea Treated with Oxytetracycline Ointment 1

| Number | Patient's Initials | BPEI # | Date Treated | Clinical Response | Comments |
|---|---|---|---|---|---|
| 1 | LP | 410606 | 1/2/97 | E | |
| 2 | HB | 393796 | 1/13/97 | E | |
| 3 | HP | 214814 | 12/23/96 | E | |
| 4 | BP | 358105 | 12/2/96 | G | mild burning |
| 5 | JS | 547453 | 1/10/97 | G | burned and stopped |
| 6 | FC | 225688 | 1/7/97 | E | |
| 7 | JI | 422804 | 1/13/97 | E | |
| 8 | RR | 401297 | 1/13/97 | E | |
| 9 | CA | 88261 | 1/27/97 | E | |
| 10 | DL | 531404 | 1/21/97 | G | mild burning |
| 11 | ES | 554804 | 12/16/96 | E | |

E = Excellent response, complete or almost complete relief of symptoms.
G = Good response, symptoms moderately, but not completed relieved Several patients who had previously used oral tetracycline stated that improvement in their symptoms was better with topically applied oxytetracycline than orally administered tetracycline. Three patients had moderate but not complete relief of symptoms. Three other patients experienced burning from the medication, one of which ceased treatment.

EXAMPLE 6

Resolution of Ocular Irritation by Administration of Topical Doxycycline Solution Moderate to complete relief of ocular irritation symptoms was also observed in 10 of 11 patients experiencing ocular irritation due to meibomian gland disease and delayed tear clearance that were treated with topical administration of a 0.025% aqueous solution of doxycycline to their eyes 3 to 4 times per day for 2 weeks. See Table 3. The solution was prepared as described herein. A reduction of corneal fluorescein staining was observed in several of these patients.

TABLE 3

Patients Treated With Topical Doxycycline

| No. | BPEI # | DIAGNOSIS | RESPONSE |
|---|---|---|---|
| 1 | 585447 | MGD, DTC | complete |
| 2 | 460606 | MGD, DTC | moderate, better than oral |
| 3 | 537137 | MGD, DTC | compete, better than oral |
| 4 | 606807 | MGD, DTC | complete |
| 5 | 590395 | MGD, DTC | complete |
| 6 | 593046 | MGD, DTC | moderate |
| 7 | 503909 | MGD, DTC | complete, better than oral |
| 8 | 558105 | MGD, DTC | moderate, not as good as oral |
| 9 | 405797 | MGD, DTC | no effect |
| 10 | 576264 | MGD, DTC | moderate |
| 11 | 562422 | MGD, DTC | complete |

MGD = Meibomian gland disease
DTC = delayed tear clearance

It should be understood that the examples and embodiments described herein are for illustrative purposes only and that various modifications or changes in light thereof will be suggested to persons skilled in the art and are to be included within the spirit and purview of this application and the scope of the appended claims.

EXAMPLE 7

Figure 5:
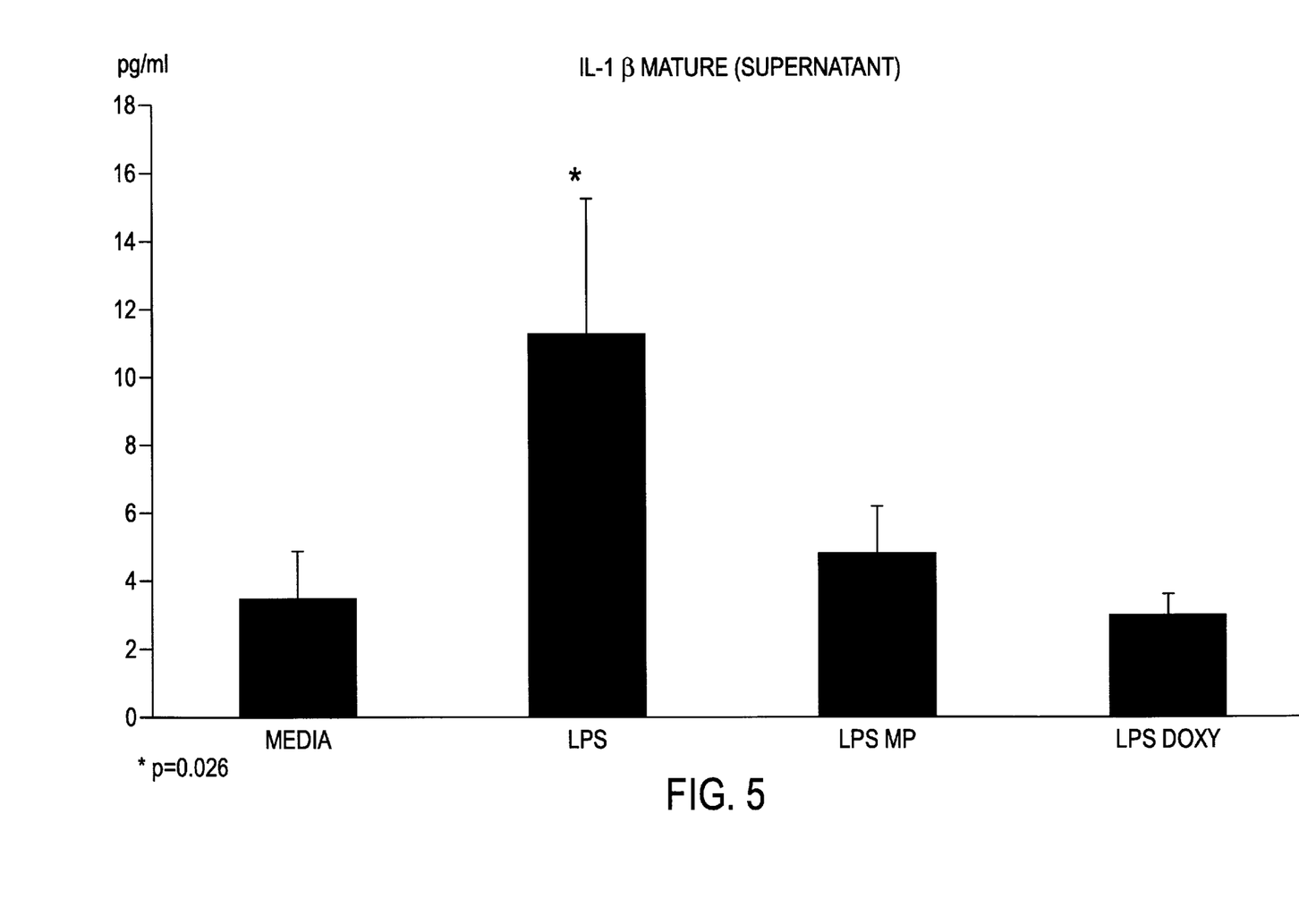
FIG. 5 shows the concentration (pg/ml) of mature IL-1α in supernatants of human corneal epithelial cell cultures.
Figure 6:
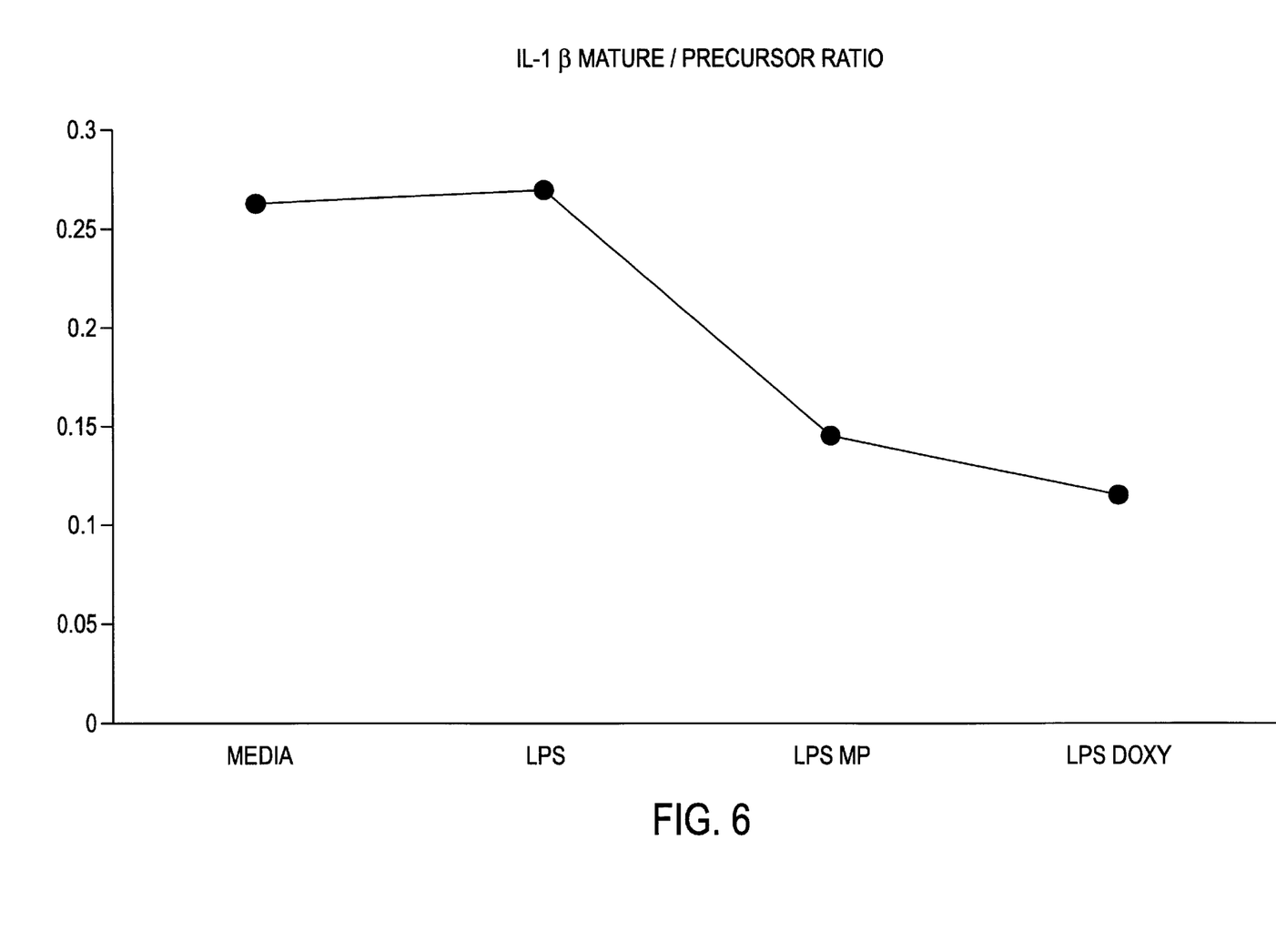
FIG. 6 shows the ratio of the mature to precursor forms of IL-1α in supernatants of human corneal epithelial cell cultures. Media=negative control; LPS=cultures treated with lipopolysaccharide for 24 h; LPS MP=cultures treated with LPS and the corticosteroid methylprednisolone for 24 h; LPS Doxy=cultures treated with LPS and doxycycline (5 µg/ml) for 24 h.

Doxycycline Inhibits the Conversion of Precursor IL-1$\beta$ to its Mature Form in Cultured Human Corneal Epithelium The effect of Doxycycline was evaluated on the concentrations of precursor and mature IL-1$\beta$ in the supernatants of human corneal epithelial cell cultures that were stimulated with lipopolysaccharide (LPS). Doxycycline significantly decreased the level of the mature biologically active form of IL-1$\beta$ compared to LPS-stimulated cultures that were not stimulated with doxycycline (FIG. 5). Furthermore, doxycycline markedly decreased the ratio of mature to precursor IL-1$\beta$ (FIG. 6). A decrease in the level of IL-1$\beta$ mRNA in doxycycline-treated cultures was also observed. These findings demonstrate that doxycycline inhibits that synthesis and activation of the inflammatory cytokine IL-1$\beta$.

EXAMPLE 8

Doxycycline Increases Release of the Anti-inflammatory Form of IL-1, IL-1RA e-1 receptor antagonist (IL-1RA) is a molecule produced by epithelial and inflammatory cells that binds to the type 1 IL-1 receptor but does not initiate signal transduction.

Figure 7:
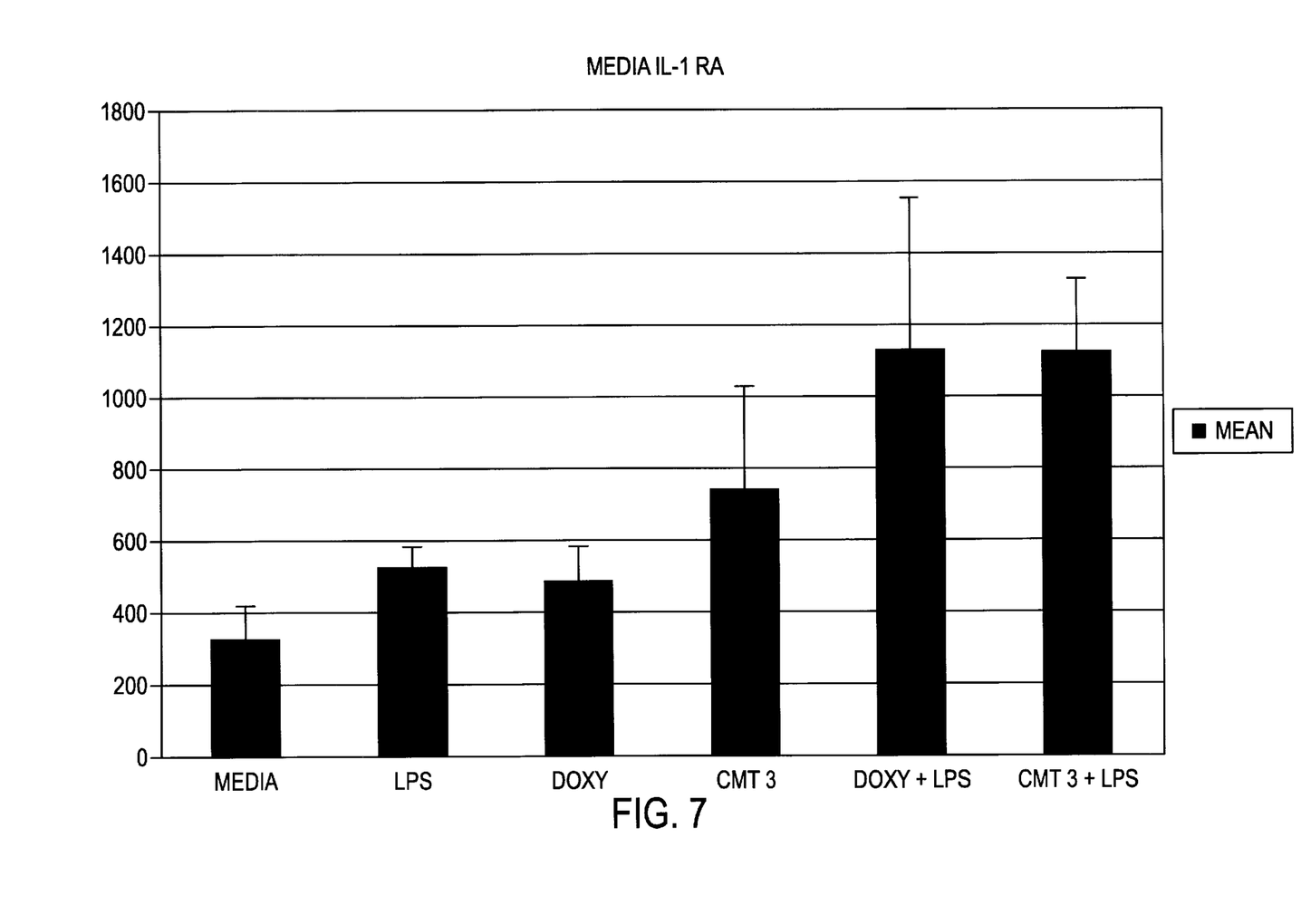
FIG. 7 shows the concentration (pg/ml) of IL-1RA in supernatants of human corneal epithelial cell cultures. Media=negative control; LPS=cultures treated with lipopolysaccharide for 24 h; Doxy=cultures treated with doxycycline (5 µg/ml) for 24 h; CMT 3=cultures treated with chemically modified tetracycline CMT 3 (1 µg/ml) for 24 hr; Doxy+LPS=cultures treated with LPS and doxycycline (5 µg/ml) for 24 h; CMT 3+LPS=cultures treated with LPS and chemically modified tetracycline CMT 3 (1 µg/ml) for 24 hr.

IL-1RA has an anti-inflammatory effect by competing with the pro-inflammatory forms of IL-1 (IL-1$\alpha$ and IL-1$\beta$) for the type 1 receptor. The addition of doxycycline or the chemically modified tetracycline CMT-3 to human corneal epithelial cell cultures significantly increased the release of IL-1RA in to the media compared to untreated cultures. Furthermore, the concentration of IL-1RA in corneal epithelial cultures stimulated with LPS and treated with either doxycycline or CMT-3 was greater than cultures exposed to LPS alone (FIG. 7). These findings indicate tetracyclines are anti-inflammatory due to their ability to stimulate IL-1RA release by the human corneal epithelium.

EXAMPLE 9

Doxycycline Decreases MMP-9 Activity in Human Corneal Epithelial Cultures

Figure 8:
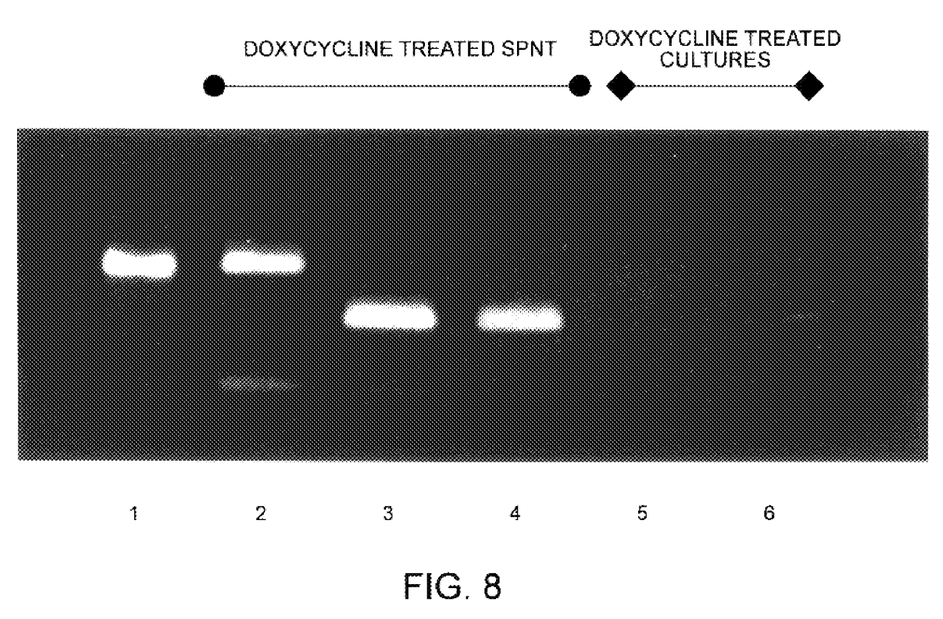
FIG. 8 is a gelatin zymogram of human corneal epithelial cell supernatant: doxycycline treatment and MMP-3 activation. Lane Legend: (1) 92 kDa purified pro-MMP-9 standard (0.1 ng); (2) Corneal epithelial supernatant+50 µg/mL doxycycline; (3)Supernatant+50 µg/mL doxycycline+1.5 ng/µL MMP-3; (4) Supernatant+100 µg/mL doxycycline+1.5 ng/µL MMP-3; (5) Supernatant from cell culture pre-treated with doxycycline; (6) Supernatant from cell culture pre-treated with doxycycline+1.5 ng/µL MMP-3.

Exposure of human corneal epithelial cultures to doxycycline (5·g/ml) for 24 hours decreased the level of pro-MMP9 activity in the supernatant by 70% compared to untreated cultures (FIG. 8). MMP-9 is the metalloproteinase responsible for initiating sterile corneal ulceration and it is also capable of cleaving precursor IL-1$\beta$ into its mature form.

All cited references are hereby incorporated herein by reference.

REFERENCES

1. Mathers W D, Lane J A, Sutphin J E, Zimmerman M B. Model for ocular tear film function. Cornea. 1996;15:110–9.
2. Browning D J, Proia A. Ocular rosacea. Surv Ophthalmol. 1986;31:145–58.
3. Jenkins M S, Brown S I, Le mpert S L, Weinberg R J. Ocular rosacea. Am.J.Ophthalmol. 1979;88:618.
4. Pflugfelder S C, Tseng S C G, Sanabria O, et al. Evaluation of subjective assessments and objective diagnostic tests for diagnosing tear-film disorders known to cause ocular irritation. Cornea. 1998;17:38.
5. Driver P J, Lemp M A. Meibomian gland dysfunction. Surv Ophthalmol. 1996;40:343–67.
6. Bartholomew R S, Reid B J, Cheesebrough M J, Macdonald M, Galloway N R. Oxytetracycline in the treatment of ocular rosacea. Br.J.Ophthalmol. 1982;66:386–8.
7. Akpek E K, Merchard A, Pinar V, Foster C S. Ocular rosacea. Patient characteristics and follow-up. Ophthalmology. 1997;104:1863–7.
8. Frucht-Pery J, Sagi E, Hemo I, Ever-Hadani P. Efficacy of doxycycline and tetracycline in ocular rosacea. Am.J.Ophthalmol. 1993;1 16:8–92.

9. Milano S, Arcoleo F, D'Agostino P, Cillari E. Intraperitoneal injection of tetracyclines protects mice from lethal endotoxemia downregulating inducible nitric oxide synthase in various organs and cytokine and nitrate secretion in blood. Antimicrob.Agents Chemother. 1997;41:117–21.
10. Amin A R, Attur M G, Thakker G D, et al. A novel mechanism of action of tetracyclines: Effects on nitric oxide synthases. Proc.Natl.Acad.Sci.U.S.A. 1996;93:14014–9.
11. Golub L M, Ramamurthy N S, McNamara T D. Tetracyclines inhibit connective tissue breakdown, new thereapeutic indications for an old family of drugs. Crit Rev Oral Biol Med. 1991;2:297–322.
12. Tilley B C, Alarcon G S, Heyse S P, et al. Minocycline in rheumatoid arthritis. A 48 week double-blind placebo-controlled trial. Ann.lnt.Med. 1995;122:81–9.
13. Seedor J A, Perry H D, McNamara T D, Golub L M, Buxton D F, Guthrie D S. Systemic tetracycline treatment of alkali-induced corneal ulceration in rabbits. Arch.Ophthalmol. 1987;105:268–71.
14. Lindhe J, Liljenberg B, Adielsson B. Effect of long-term tetracycline therapy on human periodontal disease. J Clin Periodontol. 1983;10:590–7.
15. Afonso A, Monroy D, Tseng S C G, Stern M, Pflugfelder S C. Diagnostic sensitivity and specificity of Schirmer test and fluorescein clearance test for ocular irritation. Ophthalmology. 1999; 106:803–810.
16. Barton K, Monroy D, Nava A, Pflugfelder S C. Inflammatory cytokines in tears of patients with ocular rosacea. Ophthalmology. 1997;104:1868–74.
17. Dinarello C A, Wolff S M. The role of interleukin-1 in disease. N Engl J Med 1993; 328:106–113.
18. Chouros G P. The hypothalamic-pituitary-adrenal axis and immune-mediated inflammation. N Engi J Med 1995; 332:1351–1362.
19. Yucel-Lindberg T, Nilsson S, Modeer T. Signal transduction pathways involved in the synergistic stimulation of prostaglandin production by interleukin-1 beta and tumor necrosis factor alfa in human gingival fibroblasts. J Dent Res 1999; 78:61–68.
20. Woessner J J. Matrix metalloproteinases and their inhibitors in connective tissue remodeling. FASEB J 1991; 5:2145–2155.
21. Afonso A, Sobrin L, Monroy D, Seizer M, Lokeshwar B, Pflugfelder S C. Tear fluid pro gelatinase B activity correlates with IL-1α concentration and tear clearance in patients with ocular rosacea. Invest.Ophthalmol Vis.Sci. 1999; (in press).

What is claimed is:

1. A method of treating a patient having meibomian gland disease, aqueous tear deficiency, delayed tear clearance or recurrent corneal epithelial erosion, said method comprising:
topically administering a non-antimicrobial amount of tetracycline to an eye of the patient said amount being effective to decrease inflammation associated with delayed tear clearance.

2. The method of claim 1, wherein said tetracycline is oxytetracycline.

3. The method of claim 1, wherein said tetracycline is doxycycline.

4. The method of claim 1, wherein said treatment increases tear clearance in the eye of the patient.

5. The method of claim 1, wherein said treatment comprises inhibiting a member selected from the group consisting of synthesis and activation of interleukin-1β, conversion of precursor interleukin-1β to mature interleukin-1β, ocular surface inflammation and reactive oxygen species in tear fluid and ocular surface epithelium.

6. The method of claim 1, wherein said treatment comprises increasing production of interleukin-1 receptor antagonist by corneal epithelium.

7. The method of claim 1, wherein said treatment comprises reducing interleukin-1-α concentration in tear fluid.

8. A method of treating a patient having meibomian gland disease, aqueous tear deficiency, delayed tear clearance or recurrent corneal epithelial erosion, said method comprising:
orally administering a non-antimicrobial amount of tetracycline to an eye of the patient, in an amount effective to decrease inflammation associated with delayed tear clearance.

9. The method of claim 8, wherein said treatment comprises inhibiting a member selected from the group consisting of matrix metalloproteinase activity in tear fluid, synthesis and activation of interleukin- 1β, conversion of precursor interleukin-1β to mature interleukin-1β, ocular surface inflammation and reactive oxygen species in tear fluid and ocular surface epithelium.

10. The method of claim 8, wherein said treatment comprises increasing production of an interleukin-1 receptor antagonist by corneal epithelium.

11. The method of claim 8, wherein said treatment comprises reducing interleukin-1-α concern in tear fluid.

12. A method of treating a patient having meibomian gland disease, aqueous tear deficiency, delayed tear clearance or recurrent corneal epithelial erosion, said method comprising:
topically administering a non-antimicrobial tetracycline to an eye of the patient in an amount effective to decrease inflammation associated with delayed tear clearance.

13. The method of claim 12, wherein said non-antimicrobial tetracycline is a tetracycline which lacks a dimethylamino side chain at position 4.

14. The method of claim 12, wherein said non-antibacterial tetracycline is selected from the group consisting of 4-dedimethylaminotetracycline, 4-dedimethylamino-5-oxytetracycline, 4-dedimethylamino-7-chlorotetracycline, 4-hydroxy4-dedimethylaminotetracycline, 4-dedimethylamino-12a-deoxytetracycline, 4-dedimethylamino-11-hydroxy-12a-deoxytetracycline, 4-dedimethylamino-7-dimethylaminotetracycline, 6-dimethyl-6-deoxy-4-dedimethylaminotetracycline, 6-o-deoxy-5-hydroxy4-dedimethylaminotetracycline, 11a-chlortetracycline, 12a-deoxytetracycline and 2-nitrilo analogs of tetracycline.

15. The method of claim 12, wherein said treatment increases tear clearance in the eye of the patient.

16. The method of claim 12, wherein said treatment comprises inhibiting a member selected from the group consisting of synthesis and activation of interleukin-1β, conversion of precursor interleukin-1β to mature interleukin-1β, ocular surface inflammation and reactive oxygen species in tear fluid and ocular surface epithelium.

17. The method of claim 12, wherein said treatment comprises increasing production of interleukin-1 receptor antagonist by corneal epithelium.

18. The method of claim 12, wherein said treatment comprises reducing interleukin-1-α concentration in tear fluid.

19. A method of treating a patient having meibomian gland disease, aqueous tear deficiency, delayed tear clearance or recurrent corneal epithelial erosion, said method comprising:

orally administering a non-antimicrobial tetracycline to said patient in an amount effective to decrease inflammation associated with delayed tear clearance.

20. The method of claim 19, wherein said non-antimicrobial tetracycline is a tetracycline which lacks a dimethylamino side chain at position 4.

21. The method of claim 19, wherein said non-antimicrobial tetracycline is selected from the group consisting of 4-dedimethylaminotetracycline, 4-dedimethylamino-5-oxytetracycline, 4-dedimethylamino-7-chlorotetracycline, 4-hydroxy-4-dedimethylaminotetracycline, 4-dedimethylamino-12a-deoxytetracycline, 4-dedimethylamino-11-hydroxy-12a-deoxytetracycline, 4-dedimethylamino-7-dimethylaminotetracycline, 6-dimethyl-6-deoxy-4-dedimethylaminotetracycline, 6-o-deoxy-5-hydroxy-4-dedimethylaminotetracycline, 11a-chlortetracycline, 12a-deoxytetracycline and 2-nitrilo analogs of tetracycline.

22. The method of claim 17, wherein said treatment comprises inhibiting a member selected from the group consisting of synthesis and activation of interleukin-1β, conversion of precursor interleukin-1β to mature interleukin-1β, ocular surface inflammation and reactive oxygen species in tear fluid and ocular surface epithelium.

23. The method of claim 19, wherein said treatment comprises increasing production of an interleukin-1 receptor antagonist by corneal epithelium.

24. The method of claim 19, wherein said treatment comprises reducing interleukin-1-α concentration in tear fluid.

* * * * *